(12) United States Patent
Suh et al.

(10) Patent No.: US 7,689,030 B2
(45) Date of Patent: Mar. 30, 2010

(54) METHODS AND APPARATUS FOR TESTING A COMPONENT

(75) Inventors: Ui Won Suh, Cincinnati, OH (US); Gigi Olive Gambrell, West Chester, OH (US); William McKnight, Hamilton, OH (US); Preeti Pisupati, Bangalore (IN)

(73) Assignee: General Electric Company, Schenectady, NY (US)

(*) Notice: Subject to any disclaimer, the term of this patent is extended or adjusted under 35 U.S.C. 154(b) by 1133 days.

(21) Appl. No.: 11/314,513

(22) Filed: Dec. 21, 2005

(65) Prior Publication Data

US 2007/0140546 A1    Jun. 21, 2007

(51) Int. Cl.
*G06K 9/00* (2006.01)
(52) U.S. Cl. .................... 382/149; 702/38; 324/456; 348/92
(58) Field of Classification Search .............. 382/100, 382/108, 141, 142, 143, 144, 145, 147, 149, 382/152; 702/34, 35, 38; 324/456; 348/92, 348/125, 126, 127, 128, 129, 130, 135
See application file for complete search history.

(56) References Cited

U.S. PATENT DOCUMENTS

| | | | |
|---|---|---|---|
| 5,345,514 A * | 9/1994 | Mahdavieh et al. | ......... 382/152 |
| 5,903,147 A | 5/1999 | Granger, Jr. et al. | |
| 6,469,503 B2 | 10/2002 | Trantow et al. | |
| 6,545,467 B1 | 4/2003 | Batzinger et al. | |
| 6,563,307 B2 | 5/2003 | Trantow | |
| 6,566,871 B2 | 5/2003 | Holzl | |
| 6,745,622 B2 | 6/2004 | Smith et al. | |
| 6,888,347 B2 | 5/2005 | Batzinger et al. | |
| 7,015,690 B2 | 3/2006 | Wang et al. | |
| 7,026,811 B2 | 4/2006 | Roney, Jr. et al. | |
| 7,126,329 B2 | 10/2006 | Ruzzo et al. | |
| 2002/0074996 A1 | 6/2002 | Holzl | |

FOREIGN PATENT DOCUMENTS

| | | |
|---|---|---|
| EP | 0533440 A1 | 3/1993 |
| EP | 1189058 A2 | 3/2002 |
| EP | 1710571 A1 | 4/2006 |

OTHER PUBLICATIONS

EP Search Report; Place of Search—Munich; Reference No. 162854/12118; Application No./Patent No. 06126785.2-2204; May 7, 2007; 7 pgs.
Tetsuki Taniguchi et al.; Wavelet-Based Processing of ECT Images for Inspection of Printed Circuit Board; IEEE Transactions on Magnetics, vol. 37, No. 4, Jul. 2001: pp. 2790-2793.

* cited by examiner

*Primary Examiner*—Anand Bhatnagar
(74) *Attorney, Agent, or Firm*—William Scott Andes, Esq.; Armstrong Teasdale LLP

(57) ABSTRACT

A method for inspecting a component having a surface profile that includes a local minima and a local maxima. The method includes generating a raw image of a component under test utilizing an eddy current inspection system, decomposing the raw image into a plurality of images wherein each image includes a different frequency component, and reconstructing at least one final image of the component that includes frequency components that are relevant to an eddy current flaw signal.

17 Claims, 5 Drawing Sheets

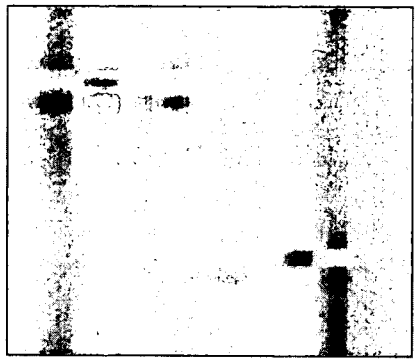
FIG. 4
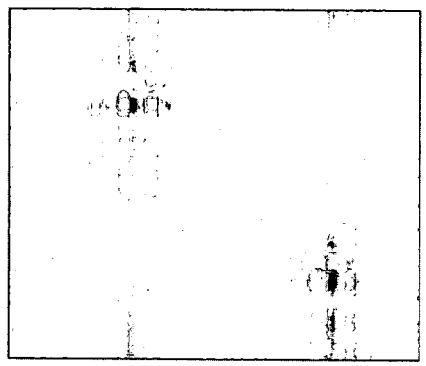
FIG. 5
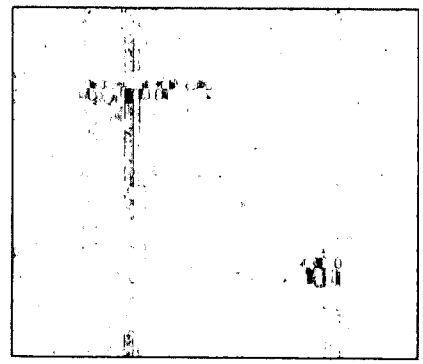
FIG. 6
FIG. 7

METHODS AND APPARATUS FOR TESTING A COMPONENT

BACKGROUND OF THE INVENTION

This invention relates generally to the testing of components, and more particularly to methods and apparatus for testing components having non-uniform surfaces.

Eddy current (EC) inspection devices are used to detect abnormal indications in a component under test such as, but not limited to, a gas turbine engine component. At least one known EC inspection device is used to detect cracks, pings, dings, raised material, and/or other surface imperfections on a surface of the component, and/or to evaluate material properties of the component including the conductivity, density, and/or degrees of heat treatment of the component.

During operation, known EC devices measure the interaction between an electromagnetic field generated by the EC device and the component being tested. For example, known EC devices include a probe coil that generates a magnetic field. When the coil is positioned adjacent to a conductive component, an eddy current is generated on the surface of the component. A flaw on and/or near the surface of the component generates a disruption in the eddy current field which produces a secondary field that is received by the eddy current probe coil or by a sensor coil in the eddy current probe which converts the altered secondary magnetic field to an electrical signal that may be recorded on a strip chart recorder for example.

While known eddy current inspection techniques are relatively effective at detecting material defects on aircraft engine components, the eddy current inspection device may be affected by a variety of conditions that the probe may encounter while inspecting the component. For example, the eddy current inspection system may generate a relatively uniform signal when the EC inspection system detects a surface crack near a uniform surface region of the component.

However, the EC inspection system may generate a spurious signal when a crack or flaw is detected near the edge of a component that includes relatively complex geometric features. Therefore, it is relatively difficult for an operator to distinguish geometric edge signals generated by the EC device when the EC device is passed over a crack and/or seam at the edge of a component. More specifically, it is often difficult for an operator to distinguish the signals generated from a real crack and/or seam from the spurious signals that may be generated near the edge of a component that has a relatively complex geometry.

As an example, at least one known EC device generates real-time images from identical, repeated geometries in a component, to facilitate improving images that include spurious signals. More specifically, a plurality of images are generated along the surface of the component, wherein each image represents only a portion of the component. After several of these images are collected, a subtraction process is utilized to extract the images from adjacent features. While this method facilitates reducing the dominant edge signals that are common to adjacent features, the method does not eliminate spurious edge signals that are caused by the geometry variations within the component. Accordingly, if only one component feature is to be inspected, the method is less effective because there are no repeated images to subtract.

BRIEF DESCRIPTION OF THE INVENTION

In one aspect, a method of inspecting a component is provided. The method includes generating a raw image of a component under test utilizing an eddy current inspection system, decomposing the raw image into a plurality of images wherein each image includes a different frequency component, and reconstructing at least one final image of the component that includes frequency components that are relevant to an eddy current flaw signal.

In another aspect, an eddy current inspection system is provided. The eddy current inspection system includes an eddy current probe, and a computer coupled to the eddy current probe. The computer is configured to generate a raw image of a feature under test, decompose the raw image into a plurality of images wherein each image includes a different frequency component, and reconstruct at least one final image of the component that includes frequency components that are relevant to an eddy current flaw signal.

BRIEF DESCRIPTION OF THE DRAWINGS

FIG. 4 is an image generated using the method in FIG. 3;
FIG. 5 is an image generated using the method in FIG. 3;
FIG. 6 is an image generated using the method in FIG. 3;
FIG. 7 is an image generated using the method in FIG. 3.

DETAILED DESCRIPTION OF THE INVENTION

Figure 1:
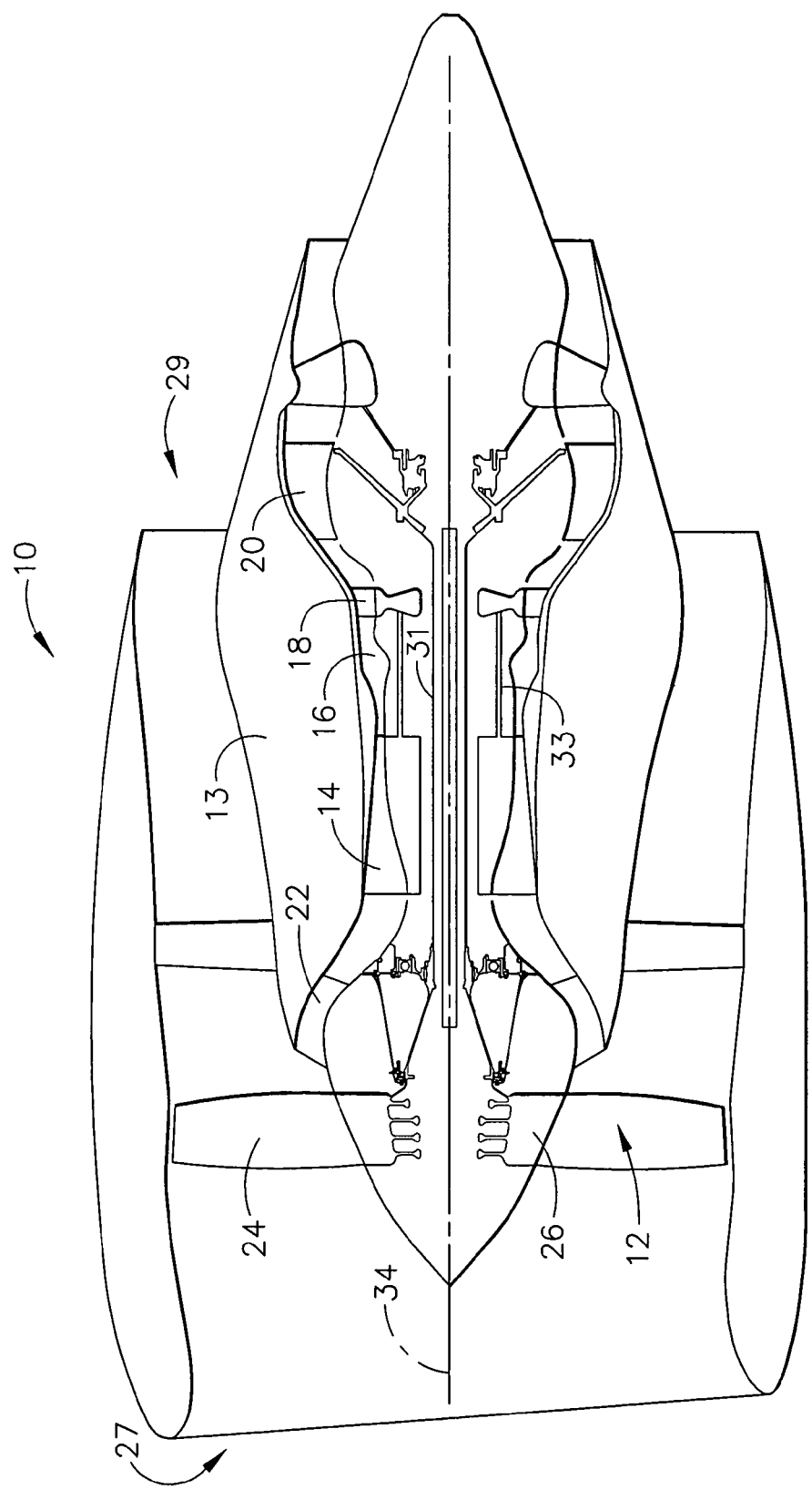
FIG. 1 is a schematic illustration of an exemplary gas turbine engine.

FIG. 1 is a schematic illustration of a gas turbine engine 10 including a fan assembly 12 and a core engine 13 including a high pressure compressor 14, and a combustor 16. Engine 10 also includes a high pressure turbine 18, a low pressure turbine 20, and a booster 22. Fan assembly 12 includes an array of fan blades 24 extending radially outward from a rotor disc 26. Engine 10 has an intake side 27 and an exhaust side 29. In one embodiment, the gas turbine engine is a CF6-50 available from General Electric Company, Cincinnati, Ohio. Fan assembly 12 and turbine 20 are coupled by a first rotor shaft 31, and compressor 14 and turbine 18 are coupled by a second rotor shaft 33.

During operation, air flows axially through fan assembly 12, in a direction that is substantially parallel to a central axis 34 extending through engine 10, and compressed air is supplied to high pressure compressor 14. The highly compressed air is delivered to combustor 16. Airflow (not shown in FIG. 1) from combustor 16 drives turbines 18 and 20, and turbine 20 drives fan assembly 12 by way of shaft 31.

Figure 2:
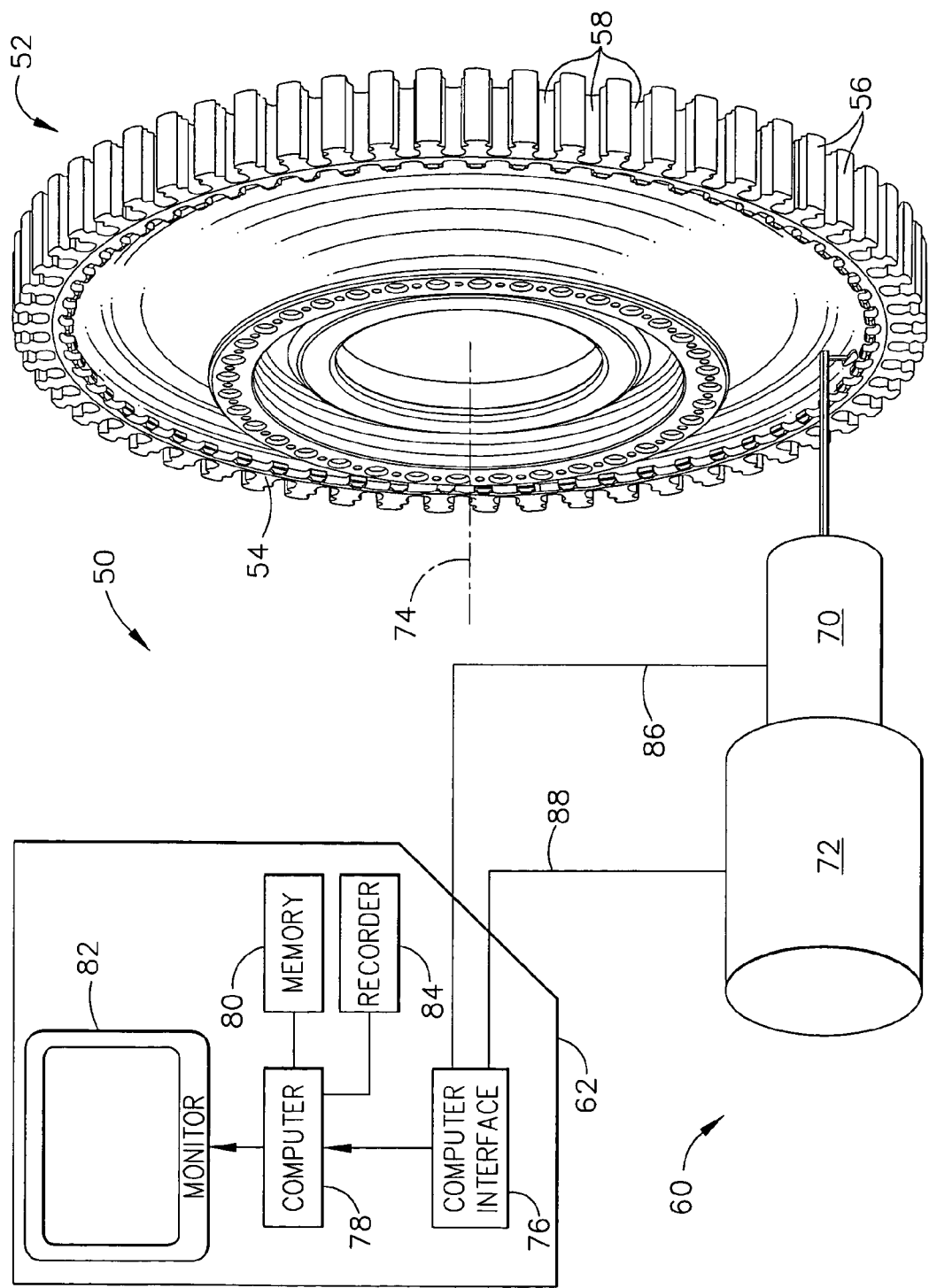
FIG. 2 is a schematic diagram of an exemplary eddy current surface flaw detection system.

FIG. 2 is a schematic diagram of an exemplary eddy current flaw detection system 50 that can be used to inspect a component 52 such as, but not limited to, a gas turbine engine disk 54 which may be used with gas turbine engine 10. In the exemplary embodiment, disk 54 includes a plurality of dovetail posts 56 and a plurality of dovetail slots 58 defined between posts 56.

Although the methods and apparatus herein are described with respect to posts 56 and dovetail slots 58, it should be appreciated that the methods and apparatus can be applied to a wide variety of components. For example, component 52 may be of any operable shape, size, and configuration. Examples of such components may include, but are not limited to, components of gas turbine engines such as seals, flanges, turbine blades, turbine vanes, and/or flanges. The component may be fabricated of any operable base material such as, but not limited to, nickel-base alloys, cobalt-base alloys, titanium-base alloys, iron-base alloys, and/or aluminum-base alloys. More specifically, although the methods and apparatus herein are described with respect to aircraft engine components, it should be appreciated that the methods and apparatus can be applied to a wide variety of components used within a steam turbine, a nuclear power plant, an automotive engine, or to inspect any mechanical components.

In the exemplary embodiment, detection system 50 includes a probe assembly 60 and a data acquisition/control system 62. Probe assembly 60 includes an eddy current coil/probe 70 and a probe manipulator 72 that is coupled to probe 70. Eddy current probe 70 and probe manipulator 72 are each electrically coupled to data acquisition/control system 62 such that control/data information can be transmitted to/from eddy current probe 70/probe manipulator 72 and data acquisition/control system 62. In an alternative embodiment, system 50 also includes a turntable (not shown) configured to rotate component 52 around a central axis 74 during the inspection procedure.

Data acquisition/control system 62 includes a computer interface 76, a computer 78, such as a personal computer with a memory 80, and a monitor 82. Computer 78 executes instructions stored in firmware (not shown). Computer 78 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Memory 80 is intended to represent one or more volatile and/or nonvolatile storage facilities that shall be familiar to those skilled in the art. Examples of such storage facilities often used with computer 78 include, but are not limited to, solid state memory (e.g., random access memory (RAM), read-only memory (ROM), and flash memory), magnetic storage devices (e.g., floppy disks and hard disks), and/or optical storage devices (e.g., CD-ROM, CD-RW, and DVD). Memory 80 may be internal to or external from computer 78. Data acquisition/control system 62 also includes a recording device 84 such as, but not limited to, a strip chart recorder, a C-scan, and an electronic recorder that is electrically coupled to either computer 78 and/or eddy current probe 70.

In use, component 52, such as disk 54, is mounted on a fixture (not shown) to secure disk 54 in place during inspection. Eddy current probe 70 is positioned within dovetail slots 58 to facilitate enabling substantially all of the interior of dovetail slots 58 to be scanned during inspection. In the exemplary embodiment, probe manipulator 72 is a six-axis manipulator. Eddy current probe 70 generates electrical signals in response to the eddy currents induced within the surface of dovetail slots 58 during scanning of dovetail slots 58 by probe 70. Electrical signals generated by probe 70 are received by data acquisition/control system 62 over a data communications link 86 and are either stored in memory 80 or recorder 84. Computer 78 is also interconnected to probe manipulator 72 by a communications link 88 to facilitate controlling the scanning of disk 54. A keyboard (not shown) is electrically coupled to computer 78 to facilitate operator control of the inspection of disk 54. In the exemplary embodiment, a printer (not shown) may be provided to generate hard copies of the images generated by computer 78.

Figure 3:
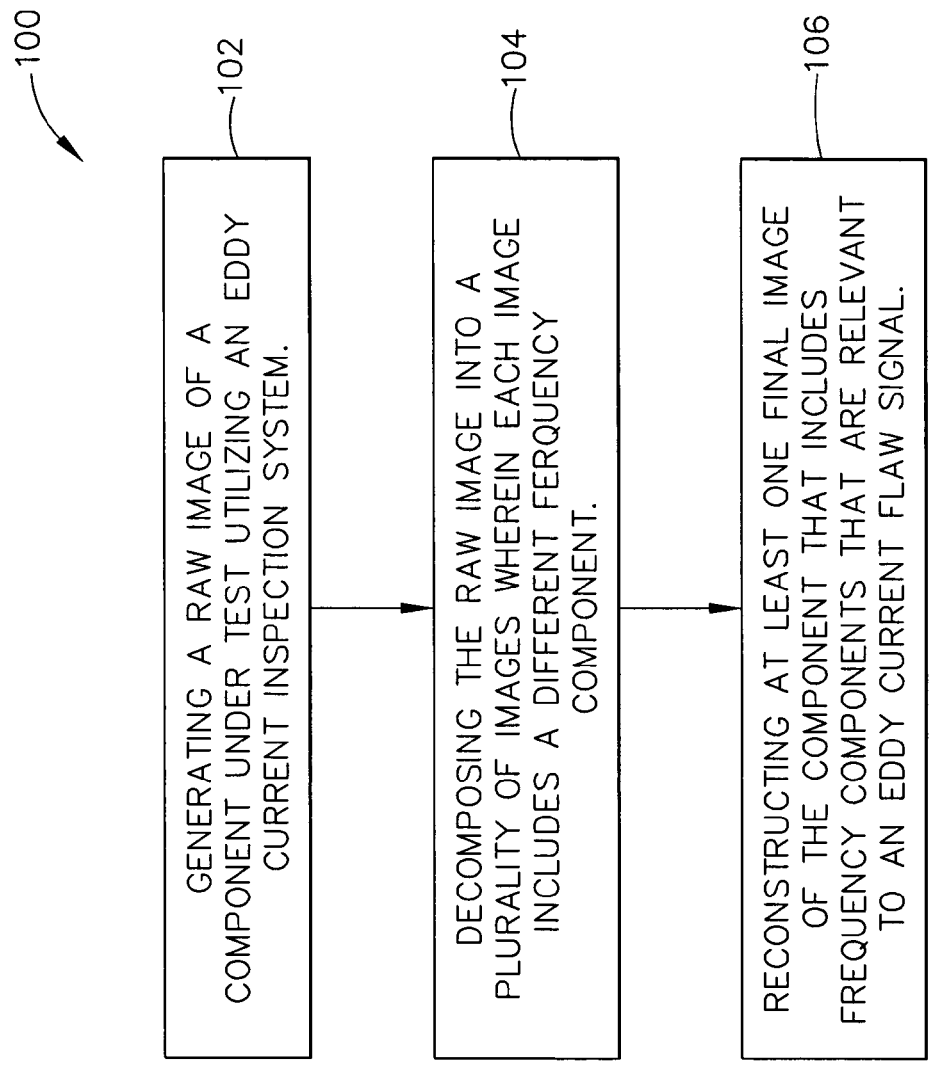
FIG. 3 is a flowchart illustrating an exemplary method for performing an eddy current inspection.

FIG. 3 is a flow chart illustrating an exemplary method 100 for inspecting a component having a surface that includes a local minima and a local maxima. Method 100 includes generating 102 a raw image, decomposing 104 the raw image into a plurality of images wherein each image includes a different frequency component, and reconstructing 106 at least one final image that includes frequency components that are relevant to an EC flaw signal.

In the exemplary embodiment, eddy current flaw detection system 50 is utilized to inspect a component 52 such as, but not limited to, a gas turbine engine disk 54 and then to generate a raw image. The raw image is then processed in a two-step procedure to facilitate identifying a crack or other flaw which may occur in component 54. Specifically, the raw image is decomposed 104 into a plurality of images wherein each image includes with different frequency components. In the exemplary embodiment, the raw image is processed utilizing a two-level Wavelet Image Processing technique. As a result of the imaging process, the raw image is decomposed into a plurality of images. In the exemplary embodiment, the raw image is decomposed into five separate images. Moreover, although the exemplary embodiment, describes decomposing the raw image into five separate images, it should be realized that the raw image may be decomposed into a desired quantity of images to facilitate identifying cracks or other defects, without affecting the scope of the invention described herein.

Figure 9:
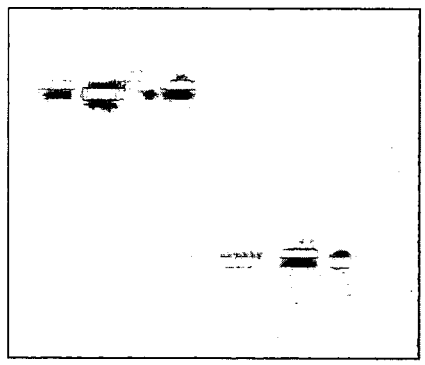
FIG. 9 is an image generated using the method in FIG. 3.

Accordingly, and in the exemplary embodiment, the raw image (shown in FIG. 4) is filtered using a low-pass convolution filter to generate a first image (shown in FIG. 5), the raw image is filtered using a high band pass filter in a horizontal direction to generate a second image (shown in FIG. 6), the raw image is filtered using a medium band pass filter in a horizontal direction to generate a third image (shown in FIG. 7), the raw image is filtered using a high band pass filter in a vertical direction to generate a fourth image (shown in FIG. 8), and the raw image is filtered using a medium band pass filter in a vertical direction to generate a fifth image (shown in FIG. 9).

Figure 8:
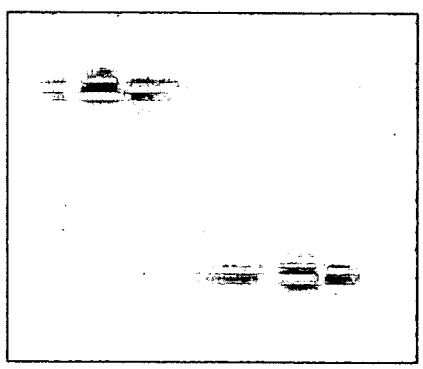
FIG. 8 is an image generated using the method in FIG. 3.

For example, as shown in FIG. 8, the component flaws are clearly visible while the edge signals are completely removed. More specifically, the image of FIG. 8 was processed utilizing a high band pass filter which facilitated removing the edge signals which generally have a lower frequency than the frequency of the signals generated by any defects within the component. Whereas, the image of FIG. 6 which was generated by processing the raw image utilizing a high band pass filter in a horizontal direction contains edge signals from which the flaw signal can not be easily segregated.

Method 100 further includes, reconstructing 106 a final image that includes frequency components that are relevant to eddy current flaw signals. More specifically, and in the exemplary embodiment, known eddy current flaw signals generally have a frequency and/or amplitude that is different than the amplitude and/or frequency of a signal that is generated due to noise or edge signals during the inspection process. These characteristics, are stored as apriori knowledge within computer 78, for example. Accordingly, computer 78 includes information of the frequency and/or amplitude of a wide variety of known flaws or defects such that during the inspection procedure, computer 78 is enabled to distinguish between a flaw signal and an edge defect and/or surrounding noise. Accordingly, computer 78 also includes apriori information of the frequency and/or amplitude characters of various signals that are generated during an eddy current inspection. The signals may include, but are not limited to, spurious edge signals that are caused by the geometry variation within the component, parameters such as probe geometry, inspection speed, flaw configuration, etc. By knowing the shape and frequency component of an eddy current flaw signal, undesirable signals can be discriminated and thus removed from the final image.

Accordingly, after the raw image has been decomposed into a plurality of images that each include a different frequency component, either computer 78 or an operator selects at least one image that is utilized to reconstruct a final image. More specifically, and in the exemplary embodiment, computer 78, utilizing the apriori knowledge, filters each generated image as explained previously, and then selects at least one image that best illustrates the eddy current flaw signal, i.e. has removed the majority of the geometry defects, etc. to reconstruct a final image.

Figure 10:
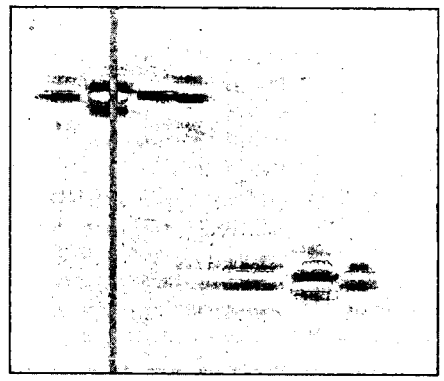
FIG. 10 is a final image generated using the method in FIG. 3.

In the exemplary embodiment, images generated in FIGS. 8 and 9 are utilized to reconstruct the final image. For example, as shown in FIG. 10, the flaw detection signals shown in FIGS. 8 and 9 are combined to generate a final image that best illustrates a flaw defect that is discovered during the inspection procedure. Accordingly, the final image is reconstructed utilizing the two frequency components observed in FIGS. 8 and 9 such that FIG. 10 has a significantly higher signal-to-noise ratio.

The method and apparatus described herein facilitates identifying characteristics in an eddy current signal that are associated with edges or other undesired geometric or contamination effects. More specifically, a mathematical model is utilized to characterize EC signals from flaws on components. During operation, the model simulates the EC signal by inputting parameters such as probe geometry, inspection speed, flaw configuration, and etc. As such, by knowing the shape and frequency component of the EC flaw signal, undesirable EC signals can be discriminated. More specifically, the segregation technique performed using a Wavelet process which decomposes the EC signals into many different signals that have different frequency characteristics. Then, those frequency components that are close to the EC flaw signal frequency are selected and all non-relevant signal frequencies from geometry, contamination, material and surface-related noise and signals are discarded. In this approach, the signal processing techniques eliminate these signals associated with unwanted features that are components of the complex, original EC signal, leaving only the flaw indications that are the target of the inspection.

Exemplary embodiments of an eddy current inspection system is described above in detail. The method described herein is not limited to the specific system described herein, but rather, the method may be practiced with a wide variety of inspection systems. More specifically, although the methods and apparatus herein are described with respect to aircraft engine components, it should be appreciated that the methods and apparatus can also be applied to a wide variety of components used within a steam turbine, a nuclear power plant, an automotive engine, or to inspect any mechanical component.

While the invention has been described in terms of various specific embodiments, those skilled in the art will recognize that the invention can be practiced with modification within the spirit and scope of the claims.

What is claimed is:

1. A method for inspecting a component having a surface profile that includes a local minima and a local maxima, said method comprising:

generating a raw image of a component under test utilizing an eddy current inspection system;

decomposing the raw image into a plurality of images wherein each image includes a different frequency component;

storing a priori flaw signal frequency data in a computer, wherein the flaw signal frequency data includes frequency components that correspond to at least one known eddy current flaw signal;

selecting at least one image of the plurality of images that includes frequency components that correspond to the at least one known eddy current flaw signal based at least partially on the stored a priori flaw signal frequency data; and reconstructing at least one final image of the component under test by utilizing the at least one selected image.

2. A method in accordance with claim 1 further comprising generating a raw image of a gas turbine engine component.

3. A method in accordance with claim 1 wherein decomposing the raw image includes decomposing the raw image utilizing a Wavelet Image Processing technique.

4. A method in accordance with claim 1 wherein decomposing the raw image further includes decomposing the raw image using at least one of a high band pass filter, a medium band pass filter, and a convolution filter.

5. A method in accordance with claim 1 further comprising discarding at least one image of the plurality of images that includes frequency components that are different than the frequency components that correspond to the at least one known eddy current flaw signal.

6. A method in accordance with claim 5 further comprising removing signals that have frequency components that are greater than the frequency components that correspond to the at least one known eddy current flaw signal from the reconstructed image.

7. A method in accordance with claim 1 further comprising storing a priori undesirable signal frequency data including frequency components that correspond to an edge defect signal and utilizing the computer to distinguish between an eddy current flaw signal and an edge defect signal.

8. A method in accordance with claim 7 further comprising storing shape and frequency components of at least one of an eddy current probe geometry and an eddy current inspection speed into the computer and removing the signals generated by the probe geometry and inspection speed from the raw image.

9. An eddy current inspection system comprising:

an eddy current probe; and a computer coupled to said eddy current probe, said computer configured to:

generate a raw image of a component under test;

decompose the raw image into a plurality of images wherein each image includes a different frequency component;

store a priori flaw signal frequency data, wherein the data includes frequency components that correspond to at least one known eddy current flaw signal;

select at least one image of the plurality of images that includes frequency components that correspond to the at least one known eddy current flaw signal based at least partially on the stored a priori flaw signal frequency data; and reconstruct at least one final image of the component under test from by utilizing the at least one selected image.

10. A system in accordance with claim 9 wherein said computer is further configured to generate a raw image of a gas turbine engine component.

11. A system in accordance with claim 9 wherein said computer is further configured to decompose the raw image utilizing a Wavelet Image Processing technique.

12. A system in accordance with claim 9 wherein said computer is further configured to decompose the raw image using at least one of a high band pass filter, a medium band pass filter, and a convolution filter.

13. A system in accordance with claim 9 wherein said computer is further configured to discard at least one image of the plurality of images that includes frequency components that are different than the frequency components that correspond to the at least one known eddy current flaw signal.

14. A system in accordance with claim 9 wherein said computer is further configured to remove signals that have frequency components that are greater than the frequency components that correspond to the at least one known eddy current flaw signal from the reconstructed image.

15. A system in accordance with claim 9 wherein said computer is further configured to store a priori undesirable signal frequency data including frequency components that correspond to an edge defect signal and utilize the stored frequency components to distinguish between an eddy current flaw signal and an edge defect signal.

16. A system in accordance with claim 9 wherein said computer is further configured to store the shape and frequency components of at least one eddy current flaw signal and reconstruct the final image based on the at least one eddy current flaw signal.

17. A system in accordance with claim 15 wherein said computer is further configured to further store shape and frequency components of at least one of an eddy current probe geometry and an eddy current inspection speed and remove the signals generated by the probe geometry and inspection speed from the raw image.

* * * * *